United States Patent [19]

Gedzelman

[11] Patent Number: 4,472,142
[45] Date of Patent: Sep. 18, 1984

[54] REMOVABLE PARTIAL DENTURE

[76] Inventor: Jesse Gedzelman, 1021 King St., Chappaqua, N.Y. 10514

[21] Appl. No.: 424,865

[22] Filed: Sep. 28, 1982

Related U.S. Application Data

[63] Continuation-in-part of Ser. No. 341,076, Jan. 20, 1982, abandoned.

[51] Int. Cl.[3] .............................................. A61C 13/28
[52] U.S. Cl. .................................................... 433/170
[58] Field of Search ................... 433/169, 170; 24/257, 24/255 R, 255 BS, 265 R; 403/313, 309, 302

[56] References Cited

U.S. PATENT DOCUMENTS

| | | | |
|---|---|---|---|
| 1,339,812 | 5/1920 | Dresch | 433/170 |
| 1,367,885 | 2/1921 | Means | 433/169 |
| 2,109,517 | 3/1938 | Xenis | 403/313 |
| 2,674,040 | 4/1954 | Lenzer | 433/170 |
| 3,305,254 | 2/1967 | Hopkins | 403/313 |

*Primary Examiner*—Robert Peshock

[57] ABSTRACT

An improved removable partial denture is provided for use in an edentulous space. The denture has a plurality of artificial teeth joined to each other on a base and an attachment means at each of the two ends of the denture for attaching the denture to the wearers abutment teeth. The improvement comprises utilizing an attachment means which includes a cylindrical pin having one end attached to the proximal surface of a crown and the other end removably retained in a hollow tubular member. The hollow tubular member is frictionally and rotatably mounted at one end in the bottom of the base of the denture which holds the artificial tooth adjacent the abutment tooth. The other end of the tubular member has an axial slot in the wall thereof, the slot being of sufficient length and width to permit the passage of the pin into the member with slight flexure of the walls of the slot. The walls of the slot thus retain the pin within the tubular member.

6 Claims, 4 Drawing Figures

REMOVABLE PARTIAL DENTURE

RELATED APPLICATIONS

This is a continuation-in-part of my U.S. Ser. No. 341,076 filed Jan. 20, 1982 entitled "Removable Partial Denture" and now abandoned. The entire disclosure of this parent application is incorporated herein by reference.

BACKGROUND OF THE INVENTION

1. Field of the Invention

This invention relates to an improvement in removable dentures and in particular to the means for securing such dentures in place.

2. Prior Art

There are many types of removable dentures and attachment means for maintaining these removable dentures in place, see for example the following U.S. Pat. Nos. 446,760 to Clowes: 1,140,566 to Boos; 1,347,555 to Reese; 1,519,505 to Noyes; 1,681,323 to Chayes; 1,742,310 to Floyd; 2,457,529 to Busby; 2,558,186 to Maniola; 2,594,200 to Muller; and 3,435,525 to Floren.

Generally, most of these attachment means for retaining the denture in place are initially expensive, fairly complicated to attach to the denture, i.e. high labor costs. Additionally, problems associated with wear or breakage are time consuming, expensive and inconvenient to repair for all parties involved, i.e. the dentist and patient.

The closest known relevant art is called the "Hader Bar and Rider" which is described in detail in the APM Sterngold brochure entitled "Precision Attachments-Studs, Bars, Posts-Attachment Courses" and associated literature. Generally, the Hader system utilizes a female rider which is immobilized in the base of a denture and a metal bar which has a round portion on the top upon which the plastic rider mates and a planer support means.

None of these aforementioned patents nor the Hader System teach or suggest the invention described and claimed herein.

OBJECTS AND SUMMARY OF THE INVENTION

It is an object of this invention to provide a simple and reliable attachment means between a removable denture and the abutment teeth which hold the denture in position.

Another object is to provide an attachment means which will securely hold the denture in place and which enables the denture to be readily and easily removed.

It is a further object to provide an attachment means which may be easily repaired when an element thereof becomes worn.

It is a further object of this invention to provide an attachment means which enables the denture to be readily and easily removed and is self adjusting so that exact alignment of the denture in the mouth is not required to obtain reliable attachment between the removable denture on the abutment teeth.

These and other objects of this invention are achieved with an improved removable partial denture for use in an edentulous space. The denture has a plurality of artificial teeth joined to each other on a base and an attachment means at each of the two ends of the denture for attaching the denture to the wearers abutment teeth. The improvement comprises utilizing an attachment means which includes a cylindrical pin having one end attached to the proximal surface, e.g. of a full cast crown and the other end removably retained in a hollow tubular member. The hollow tubular member is frictionally and rotatably mounted at one end in the bottom of the base of the denture which holds the artificial tooth adjacent the abutment tooth. The other end of the tubular member has an axial slot in the wall thereof, the slot being of sufficient length and width to permit the passage of the pin into the member with slight flexure of the walls of the slot. The walls of the slot thus retain the pin within the tubular member.

BRIEF DESCRIPTION OF THE DRAWINGS

In the accompanying drawings, one embodiment of the invention has been illustrated in which.

DETAILED DESCRIPTION OF THE INVENTION

Figure 1:
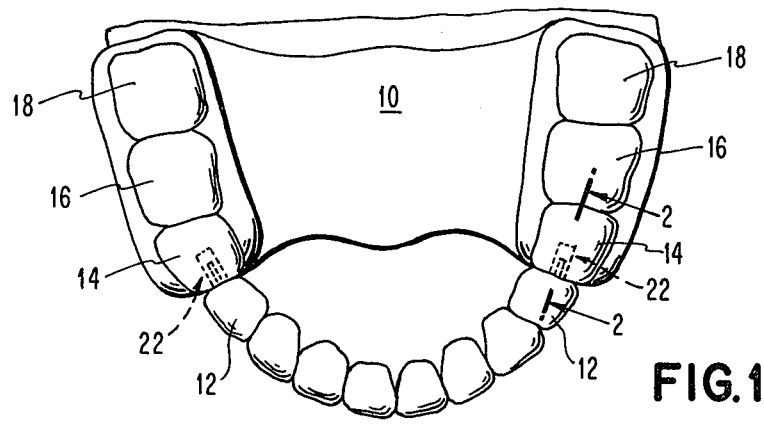
FIG. 1 is a plan view of upper teeth showing an embodiment of the improved removable partial denture in place.

Referring now to FIGS. 1-4, FIG. 1 shows the improved removable partial denture, generally designated (10). A set of natural teeth are shown, six of which have been replaced by the removable denture (10) that is illustrative of the present invention. The natural teeth that have been removed are the right and left second bi-cuspids (14) and the right and left first and second molars (16,18). Hence the abutment teeth to the edentulous area caused by the removal of these natural teeth are the left and right first bi-cuspids (12). It should be pointed out, although the denture (10) illustrated is comprised of six artificial teeth and adapts for use on the upper denture, this invention contemplates any number of teeth comprising a denture and at any location in the mouth, e.g. lower mouth, etc.

The improved removable partial denture (10) for use in the edentulous space has a plurality of artificial teeth (14, 16, 18) joined to each other on a base (20). An attachment means generally designated (22), is provided at each of the two ends of the denture (10) for attaching the denture to the wearer's abutment teeth (12).

Figure 2:
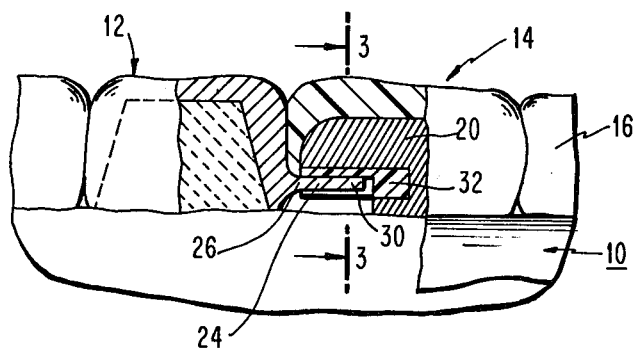
FIG. 2 is a partial section elevational view of the teeth of FIG. 1 taken along lines 2—2 of FIG. 1 showing the denture in place.
Figure 4:
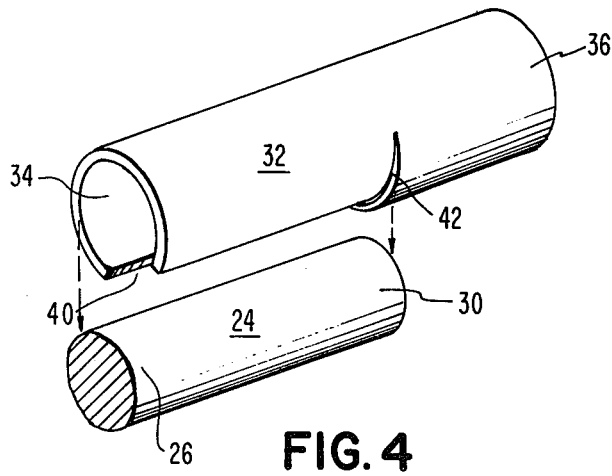
FIG. 4 is an exploded perspective view of the hollow tubular member and cylindrical pin used in the attachment means of this invention.
Figure 3:
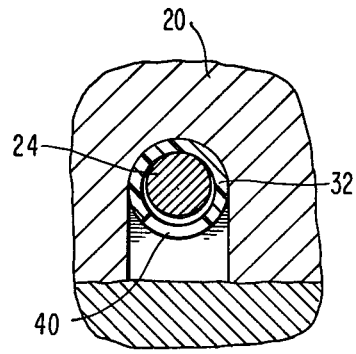
FIG. 3 is a sectional view taken along 3—3 of FIG. 2.

The improved attachment means of this invention is more clearly depicted in FIGS. 2-4. More specifically, cylindrical pin (24) is an essential part of this invention. The pin (24) is constructed of a material which is non-yielding and which will not corrode, e.g. gold, silver, palladium, etc.

The first end (26) of pin (24) is attached to the proximal surface (28) of a full cast metal crown (38) for the abutment tooth (12). Those skilled in the art are familiar with procedures for producing such crowns.

The second end (30) of pin (24), i.e. the remainder, is removably retained in a hollow tubular member (32) which is retained in the bottom of the base (20) of the denture (10). Preferably, although not necessarily, the pin (24) is frictionally retained in the hollow tubular member (32). By the use of the term "frictionally and removably retained" it is meant that the hollow tubular member (32) has inside walls (34) which grasp or engage the second end (30) of pin (24) in a manner so as to hold the denture (10) in place.

The hollow tubular member (32) is frictionally and rotatably mounted at one end (36) in the bottom of the base (20) of the denture (10). Such hollow tubular member (32) is preferably removable therefrom. The hollow tubular member (32) may be made of a polymeric material, e.g. polypropylene, polyethylene, Deldrin, etc., such materials being well known in the art.

The other end of the tubular member (32) has an axial slot (40) in the wall (34) thereof. The slot (40) is of sufficient length and width to permit the passage of the pin (24) into the tubular member (32) with slight flexure of the walls (34) of the slot (40). The inside walls (40) of the tubular member thus retain the pin (24) therein.

Preferably, as indicated more clearly in FIG. 4, the hollow tubular member (32) further comprises a radial slot means, generally designated (42) which traverses the axial slot (40). Such a radial slot means (42) enhances the flexure of the walls (34) of the axial slot (40) and additionally enhances the axial flexibility of the tubular member (32) so that during use there is a certain amount of flexibility and lack of brittleness associated with the attachment means. Preferably the radial slot means (42) comprises a radial slot which traverses the axial slot (40) at its ends for a portion of the diameter of the tubular member (32). In one embodiment produced by applicant, it was found that if 90 degrees of the tubular member (32) were removed to form the axial slot (40) then it would be desirable to have a radial slot which would extend to about 180 degrees of the hollow tubular member (see FIG. 4). Preferably as indicated in FIG. 4, the slot (42) is somewhat tapered to permit greater axial flexibility of the hollow tubing under the stress of mastication, i.e. stress breaker.

In the preferred embodiment of this invention the inside diameter of the tubular member (32) is substantially equivalent to the outside diameter of the cylindrical pin (24), although this is not a necessity as long as there is a close fit between the pin (24) and the inside walls (34) of the hollow tubular member.

One particular advantage of this attachment means is that the tubular member (32) can be easily replaced after being worn out and replaced with a new tubular member. Another advantage of this type attachment means is that the tubular member (32) is rotatable within the denture so that the slot (40) can be easily aligned on to the cylindrical pin (24). This minimizes stress on the tubular member which can lead to fracture.

Thus as can be seen from the foregoing description, the removable denture of this invention has a reliable attachment means which holds the denture in position while still permitting the denture to be readily and easily removed and inserted and which may be easily repaired when an element thereof becomes worn and cannot maintain the denture in place.

While a removable denture has been shown and described, which is illustrative of the invention, various changes in the details shown may be made within the spirit of this invention.

What is claimed is:

1. An improved removable partial denture for use in an edentulous space, the denture having a plurality of artificial teeth joined to each other on a base and an attachment means at each of the two ends of the denture for attaching the denture to the wearers abutment teeth, wherein the improvement comprises, attachment means having a cylindrical pin having one end attached to the proximal surface of a crown and the other end frictionally and removably retained in a flexible hollow tubular member, the member being frictionally, removably and rotatably mounted at one end in the bottom of the base of the denture which holds the artificial tooth adjacent the abutment tooth, the other end of the tubular member having an axial slot in the wall thereof, the slot being of sufficient length and width to permit the passage of the pin therethrough, into the member with slight flexure of the walls of the slot, the walls retaining the pin therein, whereby the denture is removably retained to the wearers abutment teeth with minimal stress thereon.

2. The removable denture of claim 1, further comprising a radial slot means traversing the axial slot for enhancing the flexure of the walls of the axial slot and enhancing axial flexibility of the tubular member.

3. The removable denture of claim 2, wherein the radial radial slot means comprises a radial slot traversing the axial slot at its end a portion of the diameter of the tubular member.

4. The removable denture of claim 3, wherein the radial slot is a tapered slot.

5. The removable denture of claim 1, wherein the tubular member is flexible polymeric material.

6. The removable denture of claim 1, wherein the inside diameter of the tubular member is substantially equal to the outside diameter of the cylindrical pin.

* * * * *